United States Patent [19]
Hayashi

[11] Patent Number: 6,002,137
[45] Date of Patent: Dec. 14, 1999

[54] FLUORESCENCE DETECTING SYSTEM

[75] Inventor: Katsumi Hayashi, Kanagawa-ken, Japan

[73] Assignee: Fuji Photo Film Co., Ltd., Kanagawa-ken, Japan

[21] Appl. No.: 09/023,206

[22] Filed: Feb. 13, 1998

[30] Foreign Application Priority Data

Feb. 13, 1997 [JP] Japan ................................. 9-0289256

[51] Int. Cl.$^6$ ............................. G01N 21/64; A61B 5/00
[52] U.S. Cl. ........................ 250/458.1; 600/476; 600/478
[58] Field of Search ............................ 250/458.1, 363.01, 250/362; 600/476, 478

[56] References Cited

U.S. PATENT DOCUMENTS

| | | | |
|---|---|---|---|
| 5,647,368 | 7/1997 | Zeng et al. | 600/476 |
| 5,833,617 | 11/1998 | Hayashi | 600/476 |

Primary Examiner—Constantine Hannaher
Assistant Examiner—Albert Gaguaroi
Attorney, Agent, or Firm—Sughrue, Mion, Zinn, Macpeak & Seas, PLLC

[57] ABSTRACT

A fluorescence detecting system detects auto fluorescence emitted from an intrinsic pigment in a part of an organism to be observed. An excitation light source projects onto the part to be observed excitation light in the wavelength range which can excite the intrinsic pigment of the organism to emit auto fluorescence. A first fluorescence detector extracts from the auto fluorescence emitted from the pigment a whole auto fluorescence component in a visible region having a predetermined wavelength range including a first relatively short wavelength range and a relatively long wavelength range. A second fluorescence detector extracts an auto fluorescence component in a second relatively short wavelength range in the visible region from the auto fluorescence. A divider carries out a division between the auto fluorescence components respectively extracted by the first and second fluorescence detector.

4 Claims, 9 Drawing Sheets

FLUORESCENCE DETECTING SYSTEM

BACKGROUND OF THE INVENTION

1. Field of the Invention

This invention relates to a fluorescence detecting system in which excitation light is projected onto a part to be observed of an organism, and then the intensity of auto fluorescence emitted from intrinsic pigment in the part is measured. Tumor is diagnosed on the basis of the intensity of the auto fluorescence measured.

2. Description of the Related Art

There have been made various investigations on photodynamic diagnosis. The photodynamic diagnosis is a technique in which a photosensitive material (ATX-S10, 5-ALA, NPe6, HAT-D01, Photofrin-2 or the like) which has affinity to tumor and emits fluorescence when excited by light is first administered to the tumor as a fluorescence diagnosis agent, excitation light having a wavelength in the exciting wavelength range of the photosensitive material is projected onto the tumor to cause the fluorescence diagnosis agent collected in the tumor, and the tumor is diagnosed on the basis of an image which is formed by the fluorescence and shows the location and the area of infiltration of the diseased part.

A fluorescence diagnosis system for carrying out such photodynamic diagnosis is disclosed, for instance, in Japanese Patent Publication No. 63(1988)-9464 and Japanese Unexamined Patent Publication Nos. 1(1989)-136630 and 7(1995)-59783. The fluorescence diagnosis system basically comprises a excitation light projecting means which projects excitation light having a wavelength in the exciting wavelength range of the photosensitive material onto an organism, an image taking means which takes a fluorescence image of the organism formed by fluorescence emitted from the photosensitive material and an image display means which displays a fluorescence image on the basis of output of the image taking means. Such a fluorescence diagnosis system is generally incorporated in an endoscope or an operative microscope.

Further there has been proposed a technique of diagnosing tumor in which excitation light having a wavelength in the exciting wavelength range of pigment inherent to an organism is projected onto the organism without administering any photosensitive material to the organism and an image of the location and the area of infiltration of the diseased part is displayed on the basis of auto fluorescence emitted from the pigment, and tumor is diagnosed on the basis of the fluorescence image.

Further there has been known a fluorescence diagnosis system in which, without taking a two-dimensional fluorescence image, the intensity of fluorescence is detected for each point on an organism and whether the point is tumor-bearing is determined according to the intensity of fluorescence. See, for instance, Japanese Unexamined Patent Publication No. 9(1997)-149891.

In such a fluorescence diagnosis system, since the surface of a part of an organism is generally uneven. the distance between the excitation light projecting means and the part to be observed differs from point to point and accordingly illuminance of the excitation light generally differs from point to point. The intensity of fluorescence is generally proportional to the illuminance of the excitation light and the illuminance of the excitation light reduces in reverse proportion to the square of the distance from the light source. Accordingly, there cases where a normal part near to the light source emits fluorescence stronger than that emitted from a diseased part remote from the light source or fluorescence from a diseased part positioned inclined to the excitation light is extremely weakened. Thus nonuniformity of illuminance of the excitation light can lead to misdiagnosis.

In order to compensate for change in intensity of fluorescence due to difference in distance from the light source, there have been proposed fluorescence diagnosis systems such as disclosed in Japanese Unexamined Patent Publication No. 62(1987)-247232, Japanese Patent Publication No. 3(1991)-58729 and the like. In the fluorescence diagnosis system disclosed in the former patent publication, excitation light is projected onto a part of an organism which has been given a photosensitive material having a strong affinity to a diseased part, emitted fluorescence and reflected excitation light are detected and image processing operation is carried out on the basis of a division between the fluorescence component and the reflected light component. By such a division, terms related to the distance from the light source can be cancelled. However since there remains a term related to the reflectance of the part exposed to the excitation light in the result of the division, there still remains a problem that a fluorescence image accurately reflecting the distribution of the fluorescence diagnosis agent cannot be obtained.

In the system disclosed in "FLUORESCENCE IMAGING OF EARLY LUNG CANCER" (Annual International Conference of the IEEE Engineering and Biology Society, Vol. 12, No. 3, 1990), auto fluorescence emitted from intrinsic pigment of a part to be observed in an organism is divided into a component having a wavelength in a green region (will be referred to as "the green region component G", hereinbelow) and a component having a wavelength in a red region (will be referred to as "the red region component R", hereinbelow), and carries out an image processing operation on the basis of division between the red region component R and the green region component G, and a result of the division is displayed. That is, since in a spectrum of auto fluorescence emitted from a diseased part, the intensity of the green region is extremely weaker than that in a spectrum of auto fluorescence emitted from a normal part, the reduction rate of the green region component G is much larger than of the red region component R in the auto fluorescence emitted from the diseased part. Accordingly by division of R/G, the fluorescence from the diseased part can be specifically extracted and an image can be formed on the basis of the extracted fluorescence. In the system, though the term of fluorescence intensity depending on the distances between the excitation light source and the part to be observed of the organism and between the fluorescence receiving section and the part to be observed of the organism can be cancelled, there is a problem that the S/N ratio becomes extremely low due to an extremely weak auto fluorescence at the diseased part.

In "Fluorescence Image Diagnosis of Cancer Using Red/Green Ratio" reported in 16-th Conference of Japanese Laser Medical Society, 1995 (Tokyo Medical College, Hamamatsu Photonix), it is proposed to strengthen red fluorescence at a diseased part by use of a fluorescence diagnosis agent which is accumulated in a diseased part and emits red fluorescence and to carry out operation of R/G. In this system, there can be obtained a fluorescence image in which the intensity of fluorescence from the diseased part is increased as compared with the system described in the aforesaid "FLUORESCENCE IMAGING OF EARLY LUNG CANCER".

By use of operation of R/G, the term of fluorescence intensity depending on the distances between the excitation light source and the part to be observed of the organism and between the fluorescence receiving section and the part to be observed of the organism can be cancelled.

However, since the green auto fluorescence at the diseased part is extremely weak, there still remains a problem that operation of R/G sometimes results in R/0, which is apt to lead to operation errors.

SUMMARY OF THE INVENTION

In view of the foregoing observations and description, the primary object of the present invention is to provide a fluorescence detecting system in which the intensity of fluorescence which depends upon the distances between the excitation light source and the part to be observed and between the fluorescence receiving means and the part to be observed can be corrected so that operation errors cannot occur.

In accordance with a first aspect of the present invention, there is provided a fluorescence detecting system for detecting auto fluorescence emitted from an intrinsic pigment in a part of an organism to be observed upon excitation by excitation light without giving any photosensitive material (fluorescence diagnosis agent) to the part, comprising an excitation light projecting means which projects onto the part to be observed excitation light in the wavelength range which can excite the intrinsic pigment of the organism to emit fluorescence, a first fluorescence detecting means which extracts from the auto fluorescence emitted from the pigment the whole auto fluorescence component in a visible region having a predetermined wavelength range including a first relatively short wavelength range and a relatively long wavelength range, a second fluorescence detecting means which extracts an auto fluorescence component in a second relatively short wavelength range in the visible region from the auto fluorescence, and a divider means which carries out a division between the auto fluorescence components respectively extracted by the first and second fluorescence detecting means.

The first and second relatively short wavelength ranges may be either the same wavelength range or different wavelength ranges.

In accordance with a second aspect of the present invention, there is provided a fluorescence detecting system for detecting auto fluorescence emitted from an intrinsic pigment in a part of an organism to be observed upon excitation by excitation light without giving any photosensitive material (fluorescence diagnosis agent) to the part, comprising an excitation light projecting means which projects onto the part to be observed excitation light in the wavelength range which can excite the intrinsic pigment of the organism to emit fluorescence, a first fluorescence detecting means which extracts from the auto fluorescence emitted from the pigment a sum fluorescence component of a fluorescence component in a predetermined short wavelength range within a visible region having a predetermined wavelength range including a first relatively short wavelength range and a relatively long wavelength range and a fluorescence component in a predetermined long wavelength range within the relatively long wavelength range in the visible region, said predetermined short wavelength range being within the first relatively short wavelength range, a second fluorescence detecting means which extracts from the auto fluorescence an auto fluorescence component in a second relatively short wavelength range in the visible region, and a divider means which carries out a division between the sum fluorescence component extracted by the first fluorescence detecting means and the fluorescence component extracted by the second fluorescence detecting means.

The first and second relatively short wavelength ranges may be either the same wavelength range or different wavelength ranges.

In both the aforesaid fluorescence detecting systems of the present invention, the first and second fluorescence detecting means need not be limited to those which detect the intensity of fluorescence for each point on the part to be observed but may be those which two-dimensionally detect the fluorescence emitted from the part to be observed and take a fluorescence image of the part.

Further each of the first and second fluorescence detecting means may detect the aforesaid fluorescence component in any manner. For example, the desired fluorescence component may be directly extracted by separating from the auto fluorescence as emitted from the pigment by use of an optical filter or the like, or may be extracted by separating the fluorescence component in a predetermined wavelength range including therein a desired fluorescence component from the auto fluorescence as emitted from the pigment and carrying out an operation processing such as addition and/or subtraction on the separated fluorescence component.

In the fluorescence detecting systems of the present invention, since a division is carried out with the whole auto fluorescence component in a visible region ranging from a relatively short wavelength range to a relatively long wavelength range or a sum fluorescence component of a fluorescence component in a relatively short wavelength range within a visible region and a fluorescence component in a relatively long wavelength range in the visible region employed as a divisor and an auto fluorescence component in a relatively short wavelength range employed as a dividend, the divisor can be sufficiently large and the possibility of dividing a value by 0 can be avoided, whereby occurrence of operation error can be prevented and the fluctuation in intensity of fluorescence due to difference in distance between the excitation light source and the part to be observed can be stably removed.

Accordingly by use of the fluorescence detecting system of the present invention in a fluorescence diagnosis system, a fluorescence image free from the fluctuation in intensity of fluorescence due to difference in distance between the excitation light source and the part to be observed can be obtained, which results in a higher diagnostic performance.

DESCRIPTION OF THE PREFERRED EMBODIMENT

Figure 1:
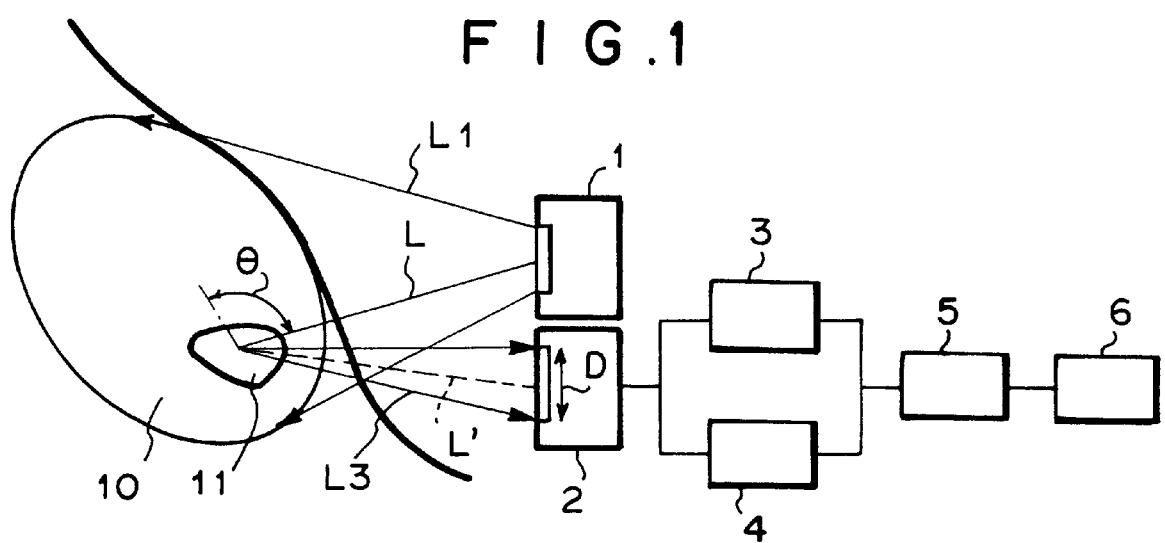
FIG. 1 is a schematic view showing a basic arrangement of a fluorescence detecting system of the present invention.

As shown in FIG. 1, the fluorescence detecting system of the present invention basically comprises an excitation light projecting means 1 which projects excitation light L1 onto a part 10 to be observed (will be referred to as "the diagnostic part", hereinbelow) of an organism, an optical condenser system 2 which condenses fluorescence L3 emitted from the diagnostic part 10 upon excitation by the excitation light L1, a first fluorescence detecting means 3 which separates a fluorescence component in a relatively short wavelength range in a visible region having a predetermined wavelength range from the fluorescence L3 condensed by the optical condenser system 2 and detects the fluorescence in the relatively short wavelength range, a second fluorescence detecting means 4 which detects the whole fluorescence component over the entire wavelength range in the visible region (or a fluorescence component equivalent to the whole fluorescence component in the visible region), and a divider means 5 which carries out a division on the basis of the outputs of the first and second fluorescence detecting means 3 and 4. The output of the divider means 5 is input into a display means 6 which displays a visible image.

A method of correcting the intensity of fluorescence which depends upon the distances between the excitation light projecting means 1 and each point of the diagnostic part 10 and between each point of the diagnostic part 10 and the fluorescence receiving section (the first and second fluorescence detecting means 3 and 4) will be described in detail, hereinbelow.

First a description will be made on a case where auto fluorescence emitted from intrinsic pigment in the diagnostic part 10 upon excitation by the excitation light L1 without giving any fluorescence diagnosis agent to the diagnostic part 10 is detected and a division is carried out between an auto fluorescence component in a relatively short wavelength range in a visible region having a predetermined wavelength range (e.g., a green component G, will be referred to as "the short wavelength component", hereinbelow) and the whole auto fluorescence component in the visible region (will be referred to as "the whole visible auto fluorescence component", hereinbelow). The whole visible auto fluorescence component as used in the division need not include all the components in the predetermined wavelength range but may only include at least a component in a part of the relatively short wavelength range and a component in a part of the relatively long wavelength range in the predetermined wavelength range. That is, the relatively short wavelength range in the predetermined wavelength range need not be identical to the wavelength range of "the short wavelength component" as used in the division.

The excitation light L1 of a wavelength $\lambda_{ex}$ is emitted from the excitation light projecting means 1 and projected onto the diagnostic part 10 including a diseased part 11. Auto fluorescence L3 is emitted from the diagnostic part 10 by an intrinsic pigment and is divided into a short wavelength component and a whole visible auto fluorescence component by a dichroic mirror, an optical filter or the like. The first fluorescence detecting means 3 detects the short wavelength component of the auto fluorescence L3 and the second fluorescence detecting means 4 detects the whole visible self-wavelength component of the same. The first and second fluorescence detecting means 3 and 4 may be either a photodetector such as a photodiode which detects the auto fluorescence L3 from point to point or those such as a CCD image taking device which two-dimensionally detects the auto fluorescence L3 and forms a fluorescence image.

Figure 2:
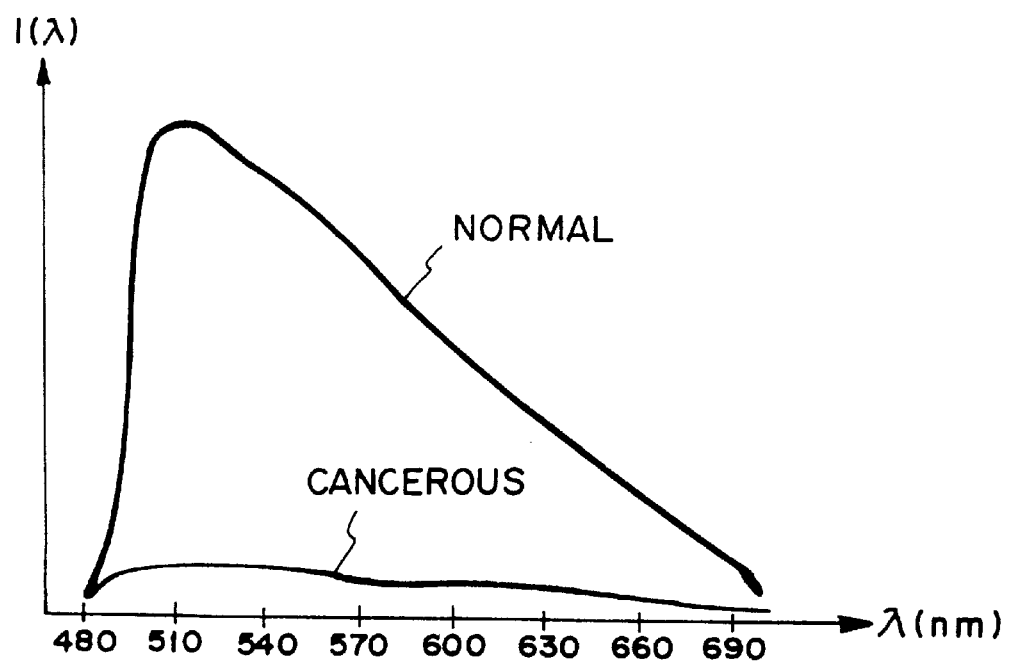
FIG. 2 is a view for illustrating a spectrum of auto fluorescence.

When the diagnostic part 10 is exposed to the excitation light L1, the diagnostic part 10 emits auto fluorescence L3 having a spectrum such as shown in FIG. 2. The auto fluorescence L3 is considered to include fluorescence emitted from various pigment in the organism such as FAD, collagen, fibronectin, porphyrin and the like. As shown in FIG. 2, the spectrum of the auto fluorescence L3 emitted from a normal part differs from that of auto fluorescence L3 emitted from a diseased part both in magnitude and shape, the reason for which has not been found. The spectrum of the auto fluorescence L3 from the normal part is large on the whole whereas the auto fluorescence L3 from the diseased part is weak on the whole. The degree by the auto fluorescence L3 from the diseased part is weakened is lower in the fluorescence component having wavelengths longer than the red region as compared with the fluorescence component in the blue to green region. That is, the ratio of the near green fluorescence component to the near red fluorescence component differs between the normal part and the diseased part. Accordingly the diseased part can be distinguished from the normal part on the basis of the aforesaid ratio of the auto fluorescence L3.

The respective components detected by the first and second fluorescence detecting means 3 and 4 are represented as follows.

The apparent short wavelength component $If\lambda_1$:

$$If\lambda_1 = k\lambda_1 \cdot I\lambda_{ex} \cdot \eta F\lambda_1 \cdot N \cdot \eta D$$

The apparent whole visible auto fluorescence component $If\lambda_2$:

$$If\lambda_2 = k\lambda_2 \cdot I\lambda_{ex} \cdot \eta F\lambda_2 \cdot n \cdot \eta D$$

wherein $\lambda_{ex}$: the wavelength of the excitation light L1, $I\lambda_{ex}$: the intensity of the excitation light L1 at the diagnostic part 10 which depends upon the distance L between the excitation light projecting means 1 and the diagnostic part 10, the power P of the excitation light projecting means 1 and the angle θ at which the light bundle of the excitation light L1 impinges upon the diagnostic part 10, $I\lambda_{ex}=I\lambda_{ex}$ (L, P, θ), n: the apparent density of the auto fluorescence molecules which contribute to the whole visible auto fluorescence component (Though the auto fluorescence molecules which contribute to auto fluorescence are considered to be of a plurality of kinds, here they may be handled to be of a single kind. In this sense, the term "apparent" is used in this specification.), N: the apparent density of the auto fluorescence molecules which contribute to the short wavelength component, $k\lambda_1$: a constant which depends upon the wavelength $\lambda_{ex}$ of the excitation light L1 and the apparent density N of the auto fluorescence molecules which contribute to the short wavelength component, $k\lambda_2$: a constant which depends upon the wavelength $\lambda_{ex}$ of the excitation light L1 and the apparent density N of the auto fluorescence molecules which contribute to the whole visible auto fluorescence component, $\eta F\lambda_1$: the fluorescence quantum yield to the wavelength $\lambda_{ex}$ of the excitation light L1 of the auto fluorescence molecules which contribute to the short wavelength component, $\eta F\lambda_2$; the fluorescence quantum yield to the wavelength $\lambda_{ex}$ of the excitation light L1 of the auto fluorescence molecules which contribute to the whole visible auto fluorescence component, ηD: the fluorescence detecting efficiency which depends upon the distance L' between a point on the diagnostic part 10 and the fluorescence detecting system, the aperture D of the fluorescence detecting system and the efficiency ξ of the detector, ηD=ηD (L', ξ, D), (though, strictly speaking, the detecting efficiency for the short wavelength component differs from that for the whole visible auto fluorescence component, they may be handled to be approximately equal to each other here).

Then the divider means 5 divides the apparent short wavelength component $If\lambda_1$ by the apparent whole visible auto fluorescence component $If\lambda_2$. That is, $$If\lambda_1/If\lambda_2=(k\lambda_1\cdot\eta F\lambda_1\cdot N)/(k\lambda_2\cdot\eta F\lambda_2\cdot n)$$

When $$(k\lambda_1\cdot\eta F\lambda_1)/(k\lambda_2\cdot\eta F\lambda_2)=C,\ N/n=X,$$

$$If\lambda_1/If\lambda_2=CX.$$

Figure 3:
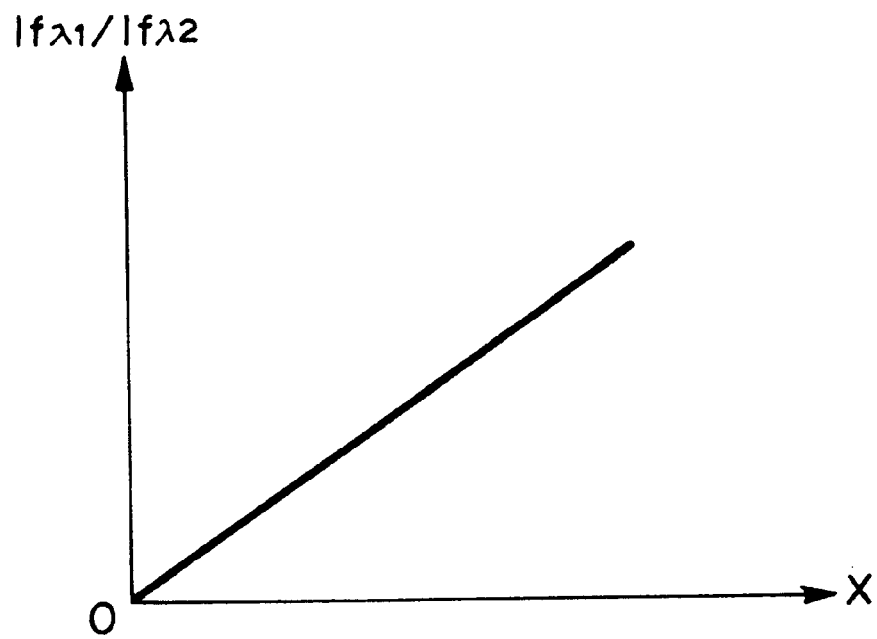
FIG. 3 is a view for illustrating the relation between the value of $If\lambda_1$ (short wavelength component)/$If\lambda_2$ (the whole visible auto fluorescence component) and a variable N/n=X obtained by standardizing the number of the fluorescent molecules which contribute to the short wavelength component by the number of the fluorescent molecules which contribute to the whole visible auto fluorescence component.

Since C is a constant, $If\lambda_1/If\lambda_2$ can be plotted as shown in FIG. 3. That is, nonuniformity in the illuminance $I\lambda_{ex}$ of the excitation light L1 from place to place can be cancelled. The value of X represents the number of the fluorescent molecules which contribute to the short wavelength component standardized by the number of the fluorescent molecules which contribute to the whole visible auto fluorescence component, and accordingly that $If\lambda_1/If\lambda_2$ is small means that the part is diseased. Thus carrying out a division between the short wavelength component $If\lambda_1$ and the whole visible auto fluorescence component $If\lambda_2$, a diseased part can be specifically extracted. At this time by employing the whole visible auto fluorescence component $If\lambda_2$ as a divisor, the divisor can be sufficiently large and the possibility of dividing a value by 0 can be avoided, whereby occurrence of operation error can be prevented. When image taking devices are employed as the first and second fluorescence detecting means 3 and 4, a fluorescence image whose fluorescence intensity is corrected can be displayed as a visible image by the display means 6.

Now a description will be made on a case where auto fluorescence emitted from intrinsic pigment in the diagnostic part 10 upon excitation by the excitation light L1 without giving any fluorescence diagnosis agent to the diagnostic part 10 is detected and a division is carried out between a short wavelength component (e.g., a green component G) and a sum fluorescence component of an auto fluorescence component in a relatively short wavelength range in the visible region and an auto fluorescence component in a relatively long wavelength range in the visible region (e.g., G+R). The short wavelength component as used in the division need not be equal to the relatively short wavelength range in the predetermined wavelength range of the visible region.

The excitation light L1 of a wavelength $\lambda_{ex}$ is emitted from the excitation light projecting means 1 and projected onto the diagnostic part 10 including a diseased part 11. Auto fluorescence L3 is emitted from the diagnostic part 10 by an intrinsic pigment and is divided into a short wavelength component and a sum fluorescence component of an auto fluorescence component in a relatively short wavelength range in the visible region and an auto fluorescence component in a relatively long wavelength range in the visible region by a dichroic mirror, an optical filter or the like. The first fluorescence detecting means 3 detects the short wavelength component of the auto fluorescence L3 and the second fluorescence detecting means 4 detects the sum fluorescence component.

The means for detecting the short wavelength component and the sum fluorescence component need not be limited to those described above. For example, the desired fluorescence component may be extracted by separating the fluorescence component in a predetermined wavelength range including therein a desired fluorescence component from the auto fluorescence as emitted from the pigment and carrying out an operation processing such as addition and/or subtraction on the separated fluorescence component. More specifically, the auto fluorescence as emitted is separated into a component in a relatively short wavelength range and a component in a relatively long wavelength range and the former and latter components are detected respectively by the first and second fluorescence detecting means 3 and 4. Then the outputs of the first and second fluorescence detecting means 3 and 4 are added to obtain the sum fluorescence component. Otherwise, the auto fluorescence as emitted is separated into a component in a relatively long wavelength range and a sum component of a component in a relatively long wavelength range and a component in a relatively short wavelength range and the former and latter components are detected respectively by the first and second fluorescence detecting means 3 and 4. Then, the output of the first fluorescence detecting means 3 is subtracted from the output of the second fluorescence detecting means 4 to obtain the short wavelength component.

The respective components detected by the first and second fluorescence detecting means 3 and 4 are represented as follows.

The apparent short wavelength component $If\lambda_1$:

$$If\lambda_1=k\lambda_1\cdot I\lambda_{ex}\cdot\eta F\lambda_1\cdot N\cdot\eta D$$

The apparent long wavelength component $If\lambda_2$:

$$If\lambda_2 = k\lambda_2 \cdot I\lambda_{ex} \cdot \eta F\lambda_2 \cdot n \cdot \eta D$$

wherein $\lambda_{ex}$ the wavelength of the excitation light L1, $I\lambda^{ex}$: the intensity of the excitation light L1 at the diagnostic part 10 which depends upon the distance L between the excitation light projecting means 1 and the diagnostic part 10, the power P of the excitation light projecting means 1 and the angle θ at which the light bundle of the excitation light L1 impinges upon the diagnostic part 10, $I\lambda_{ex} = I\lambda_{ex}$ (L, P, θ), n: the apparent density of the auto fluorescence molecules which contribute to the long wavelength component. (Though the auto fluorescence molecules which contribute to auto fluorescence are considered to be of a plurality of kinds, here they may be handled to be of a single kind. In this sense, the term "apparent" is used in this specification.), N; the apparent density of the auto fluorescence molecules which contribute to the short wavelength component, $k\lambda_1$: a constant which depends upon the wavelength $\lambda_{ex}$ of the excitation light L1 and the apparent density N of the auto fluorescence molecules which contribute to the short wavelength component, $k\lambda_2$: a constant which depends upon the wavelength $\lambda_{ex}$ of the excitation light L1 and the apparent density N of the auto fluorescence molecules which contribute to the long wavelength component, $\eta F\lambda_1$: the fluorescence quantum yield to the wavelength $\lambda_{ex}$ of the excitation light L1 of the auto fluorescence molecules which contribute to the short wavelength component, $\eta F\lambda_2$: the fluorescence quantum yield to the wavelength $\lambda_{ex}$ of the excitation light L1 of the auto fluorescence molecules which contribute to the long wavelength component, $\eta D$: the fluorescence detecting efficiency which depends upon the distance L' between a point on the diagnostic part 10 and the fluorescence detecting system, the aperture D of the fluorescence detecting system and the efficiency ξ of the detector, $\eta D = \eta D$ (L', ξ, D), (though, strictly speaking, the detecting efficiency for the short wavelength component differs from that for the long wavelength component, they may be handled to be approximately equal to each other here).

Then the divider means 5 divides the short wavelength component by the sum fluorescence component $(If\lambda_1 + If\lambda_2)$. That is, $$If\lambda_1/(If\lambda_1 + If\lambda_2) = (k\lambda_1 \cdot \eta F\lambda_1 \cdot N)/(k\lambda_1 \cdot \eta F\lambda_1 \cdot N + k\lambda_2 \cdot \eta F\lambda_2 \cdot n)$$

When $$(k\lambda_1 \cdot \eta F\lambda_1)/(k\lambda_2 \cdot \eta F\lambda_2) = C, \; N/n = X, \; If\lambda_1/(If\lambda_1 + If\lambda_2) = C \cdot X/(C \cdot X + 1).$$

Figure 4:
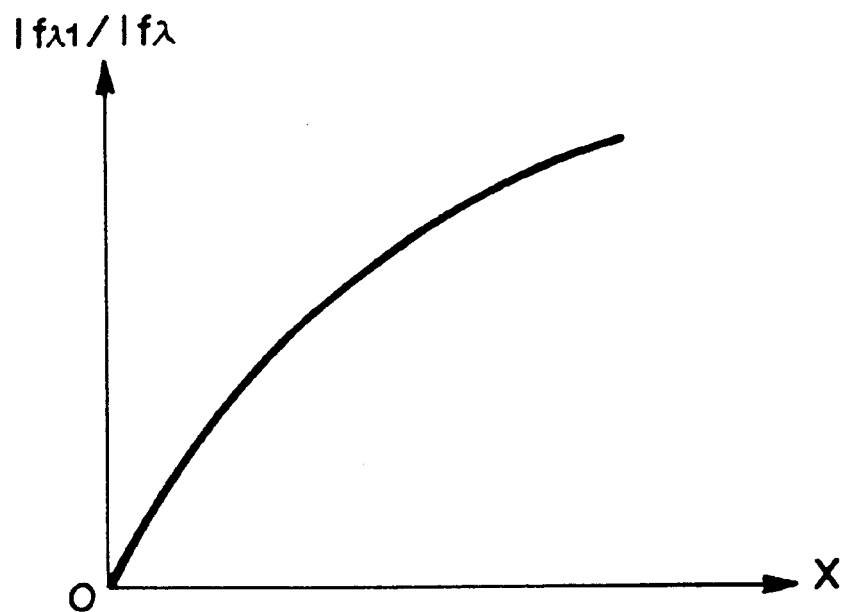
FIG. 4 is a view for illustrating the relation between the value of $If\lambda_1$ (short wavelength component)/$If\lambda_2$ (the sum fluorescence component) and a variable N/n=X obtained by standardizing the number of the fluorescent molecules which contribute to the short wavelength component by the number of the fluorescent molecules which contribute to the sum fluorescence component.

Since C is a constant, $If\lambda_1/(If\lambda_1 + If\lambda_2)$ can be plotted as shown in FIG. 4. That is, nonuniformity in the illuminance $I\lambda_{ex}$ of the excitation light L1 from place to place can be cancelled. The value of X represents the number of the fluorescent molecules which contribute to the short wavelength component standardized by the number of the fluorescent molecules which contribute to the long wavelength component, and accordingly that $If\lambda_1/(If\lambda_1 + If\lambda_2)$ is small means that the part is diseased. Thus carrying out a division between the short wavelength component $If\lambda_1$ and the sum fluorescence component $(If\lambda_1 + If\lambda_2)$, a diseased part can be specifically extracted. At this time by employing the sum fluorescence component $(If\lambda_1 + If\lambda_2)$ as a divisor, the divisor can be sufficiently large and the possibility of dividing a value by 0 can be avoided, whereby occurrence of operation error can be prevented. When image taking devices are employed as the first and second fluorescence detecting means 3 and 4, a fluorescence image whose fluorescence intensity is corrected can be displayed as a visible image by the display means 6.

Now an example of an endoscope system provided with a fluorescence diagnosis system in accordance with the present invention will be described with reference to FIGS. 5, 6, 7A and 7B, hereinbelow. In this example, auto fluorescence emitted from intrinsic pigment in the diagnostic part 10 upon excitation by the excitation light L1 without giving any fluorescence diagnosis agent to the diagnostic part 10 is detected and a division is carried out between a green auto fluorescence component and the whole visible auto fluorescence component.

Figure 5:
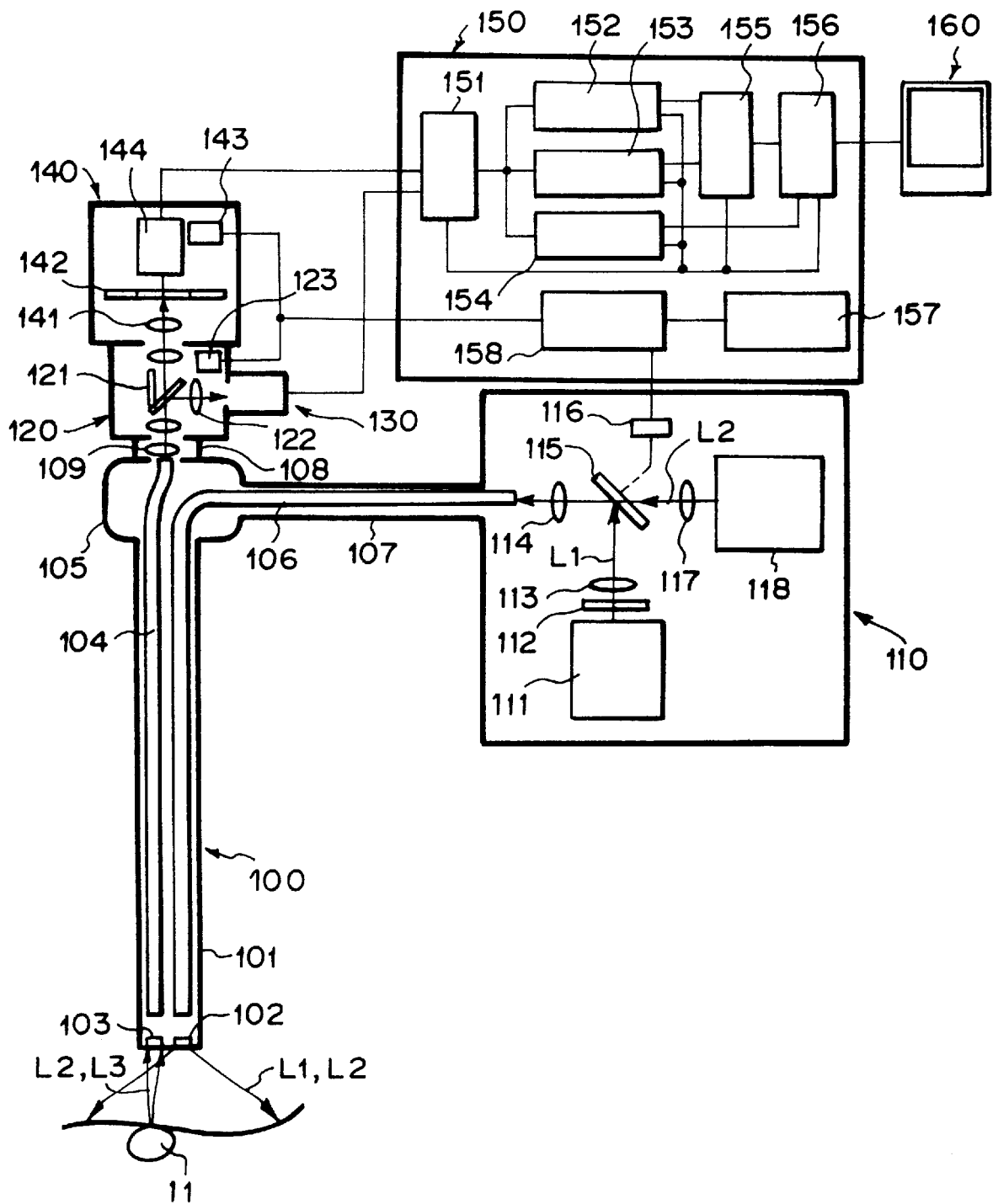
FIG. 5 is a schematic view showing an example of an endoscope system provided with a fluorescence detecting system in accordance with the present invention.
Figure 6:
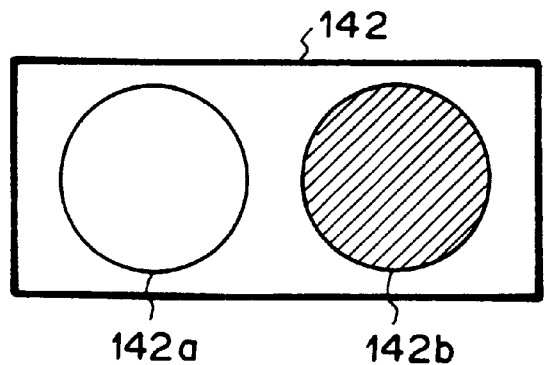
FIG. 6 is a view showing the switching optical filter employed in the endoscope system.

In FIG. 5, an endoscope system comprises an endoscope 100 which is inserted into a part of a patient which is to be observed, an illumination system 110 having an illuminating light source for emitting white illuminating light for a normal image and an excitation light source for emitting an excitation light, an optical path change-over unit 120 for switching the optical path between that for a normal image and that for a fluorescence image, a color CCD camera 130 which receives the white illuminating light reflected by the diagnostic part when a normal image is to be observed, a high speed camera unit 140 which receives fluorescence emitted from the diagnostic part upon excitation by the excitation light when a fluorescence image is to be observed, an image processing system 150 for processing the reflected light image or the fluorescence image, and a display 160 which reproduces the processed image information as a visible image.

The endoscope 100 comprises a light guide 106 and an image fiber 104 extending through an insertion portion 101 to the tip thereof. An illumination lens 102 and an objective lens 103 are disposed on the tip of the insertion portion 101. An end portion of the light guide 106 extends to the illumination system 110 through a connection 107 which connects a control section 105 and the illumination system 110. An end portion of the image fiber 104 extends to the control section 105 and is in contact with an eyepiece unit 108 having an eyepiece 109.

The illumination system 110 comprises a xenon lamp 118 which emits white light L2 for observing the normal image, a mercury-vapor lamp 111 which emits excitation light L1 for observing the fluorescence image, an optical filter 112 which transmits a selected wavelength range component of the excitation light L1 emitted from the mercury-vapor lamp 111, and a change-over mirror 115 which is driven by a driver 116 to selectively introduce the white light L2 or the excitation light L1 to the light guide 106.

The optical path change-over unit 120 is provided with a change-over mirror 121 which is driven by a driver 123 to selectively connect the image fiber 104 to the color CCD camera 130 or the high speed camera unit 140 so that the reflected light transmitted through the image fiber 104 is led to the CCD camera 130 when a normal image is to be observed and the fluorescence L3 transmitted through the image fiber 104 is led to the high speed camera unit 140 when a fluorescence image is to be observed.

The high speed camera unit 140 comprises a switching optical filter 142 which has a long pass filter 142a (FIG. 6) transmitting the whole visible auto fluorescence component and a band pass filter 142b transmitting a near-green fluorescence component and is driven by a driver 143 to insert one of the filters 142a and 142b into the path of the fluorescence L3 emanating from the image fiber 104, and a cooled CCD camera 144 on which the fluorescence L3 transmitted through the filter 142a or 142b is focused.

The image processing system 150 comprises an A/D convertor 151 which digitizes an image signal from the color CCD camera 130, a normal image memory 154 which stores the digitized normal image signal, a near-green fluorescence image memory 152 which stores a digitized image signal reflecting the near-green fluorescence component, a whole visible auto fluorescence image memory 153 which stores a digitized image signal reflecting the whole visible auto fluorescence component, a divider memory 155 which divides the output of the near-green fluorescence image memory 152 by the output of the whole visible auto fluorescence image memory 153 and stores the result of the division, a video signal generating circuit 156 which carries out an image processing on the image signals stored in the normal image memory 154 and the divider memory 155 in order to display an image on the basis of the image signals, a timing controller 158 which outputs signals to the drivers 116, 123 and 143 for the illumination system, the high speed camera unit 140 and the optical path change-over unit 120, and a video processor 157 which controls the timing controller 158.

Operation of the endoscope system will be described hereinbelow.

When a normal image is to be observed, the change-over mirror 115 is moved by the driver 116 under the control of a signal from the timing controller 158 to the position shown by the broken line, where it permits the white light L2 from the xenon lamp 118 to pass through. The white light L2 emitted from the xenon lamp 118 travels through a-lens 117 and caused to enter the light guide 106 by a lens 114. The white light L2 propagates through the light guide 106 and emanates from the front end of the light guide 106 to illuminate the diagnostic part 10 including the diseased part 11 through an illuminator lens 102.

A part of the white light L2 reflected by the diagnostic part 10 is condensed by the objective lens 103 and travels toward the change-over mirror 121 in the change-over unit 120 through the image fiber 104 and the eyepiece 109 of the eyepiece unit 108.

The change-over mirror 121 is driven by the driver 123 under the control of a signal from the timing controller 158 and is moved to the position shown by the solid line when a normal image is to be observed. The reflected light is reflected by the mirror 121 and focused on the color CCD camera 130 by a lens 122.

The red, green and blue image signals from the color CCD camera 130 are input into the A/D convertor 151 and digitized. The digitized red, green and blue image signals are stored in the corresponding normal image memories 154. The normal image signals stored in the normal image memories 154 are subjected to a color matrix processing and an encoding processing after D/A conversion by the video signal generating circuit 156, and then input into the display 160 as NTSC signals to be reproduced as a visible image by the display 160.

The aforesaid series of actions are carried out under the control of the video processor 157 and the timing controller 158.

When a fluorescence image is to be observed, the change-over mirror 115 is moved by the driver 116 under the control of a signal from the timing controller 158 to the position shown by the solid line, where it cuts the white light L2 from the xenon lamp 118 and reflects the excitation light L1. The excitation light L1 emitted from the mercury-vapor lamp 111 travels through the optical filter 112 and a lens 113 to impinge upon the change-over mirror 115. The excitation light L1 reflected by the change-over mirror 115 is caused to enter the light guide 106 by the lens 114 and propagates through the light guide 106. Then the excitation light L1 emanates from the front end of the light guide 106 and is projected onto the diagnostic part 10 including the diseased part 11 by the illuminator lens 102. The optical filter 112 transmits a bright-line spectrum having a central wavelength of 405 nm.

Fluorescence L3 emitted by the diagnostic part 10 upon excitation by the excitation light L1 is condensed by the objective lens 103 and travels toward the change-over mirror 121 in the change-over unit 120 through the image fiber 104 and the eyepiece 109 of the eyepiece unit 108.

Figure 7A:
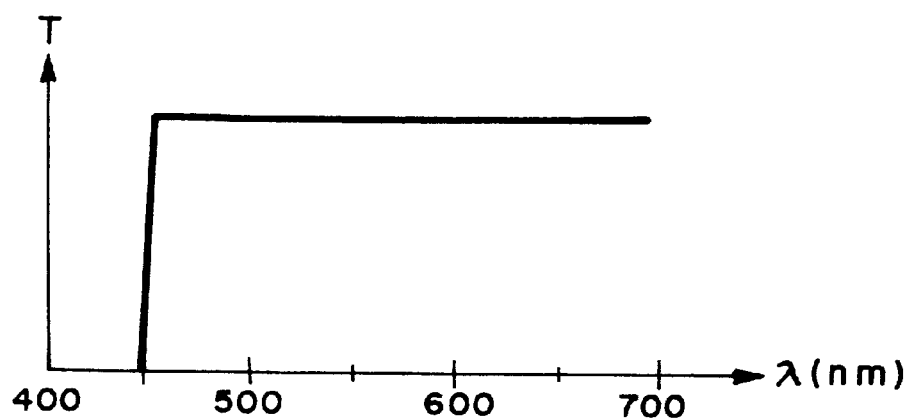
FIGS. 7A and 7B show the transmission characteristics of the filters of the switching optical filter.
Figure 7B:
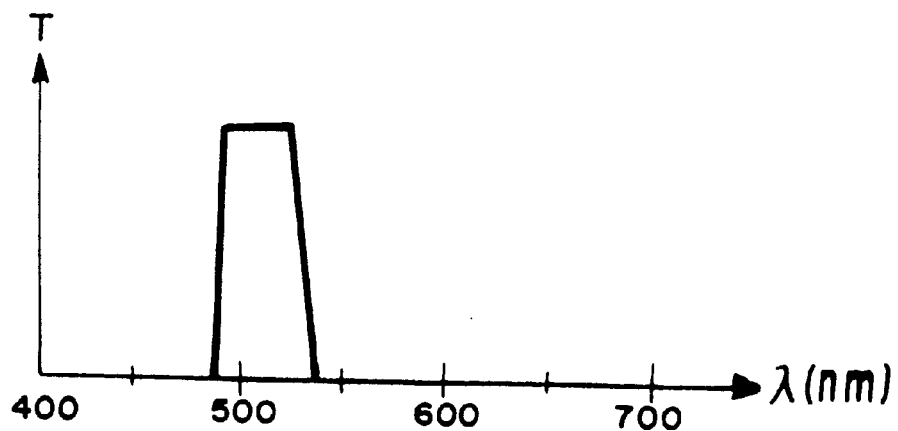

The change-over mirror 121 is driven by the driver 123 under the control of a signal from the timing controller 158 and is moved to the position shown by the broken line not to interrupt the fluorescence L3. The fluorescence L3 passes by the mirror 121 and is focused on the cooled CCD camera 144 through a lens 141 and the switching optical filter 142. As described above, the switching optical filter 142 has the long pass filter 142a and the band pass filter 142b. As shown in FIG. 7A, the long pass filter 142a transmits the whole visible auto fluorescence component having wavelengths not shorter than 460 nm and as shown in FIG. 7B, the band pass filter 142b transmits a near-green fluorescence component having wavelengths in the range of 510±10 nm.

The driver 143 first inserts the long pass filter 142a to the optical path of the fluorescence L3, whereby an image signal reflecting the whole visible auto fluorescence component is input from the cooled CCD camera 144 to the A/D convertor 151. The image signal digitized by the A/D convertor 151 is stored in the whole visible auto fluorescence image memory 153.

Thereafter the driver 143 inserts the band pass filter 142b to the optical path of the fluorescence L3, whereby an image signal reflecting the near-green fluorescence component is input from the cooled CCD camera 144 into the A/D convertor 151. The image signal digitized by the A/D convertor 151 is stored in the near-green fluorescence image memory 152.

The divider memory 155 divides the image signal reflecting the near-green fluorescence component stored in the near-green fluorescence image memory 152 by the image signal reflecting the whole visible auto fluorescence component stored in the whole visible auto fluorescence image memory 153 and stores the divided image signal. The divided image signal stored in the divider memory 155 is subjected to an encoding processing by the video signal generating circuit 156 after D/A conversion and then input into the display 160 to be reproduced as a visible image by the display 160. The normal image and the divided image may be overlaid.

Figure 8:
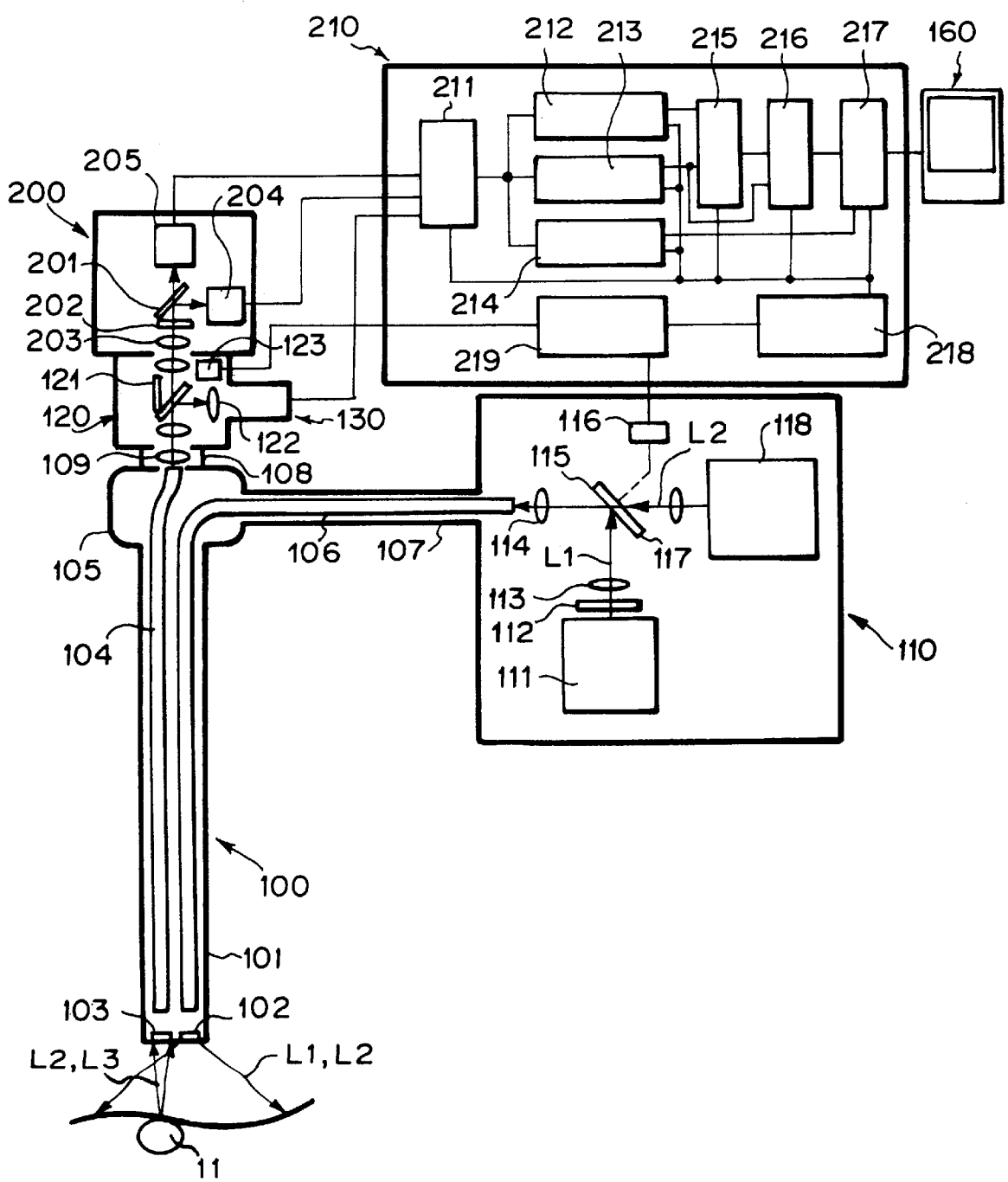
FIG. 8 is a schematic view showing another example of an endoscope system provided with a fluorescence detecting system in accordance with the present invention, FIGS. 9A and 9B respectively show the transmission characteristics of the long pass filter and the dichroic mirror.
Figure 9A:
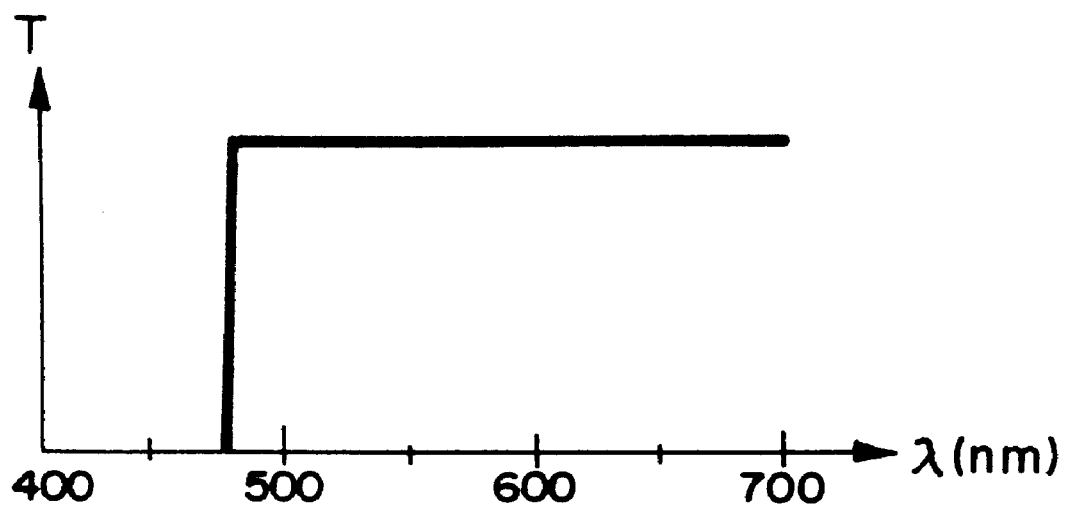
Figure 9B:
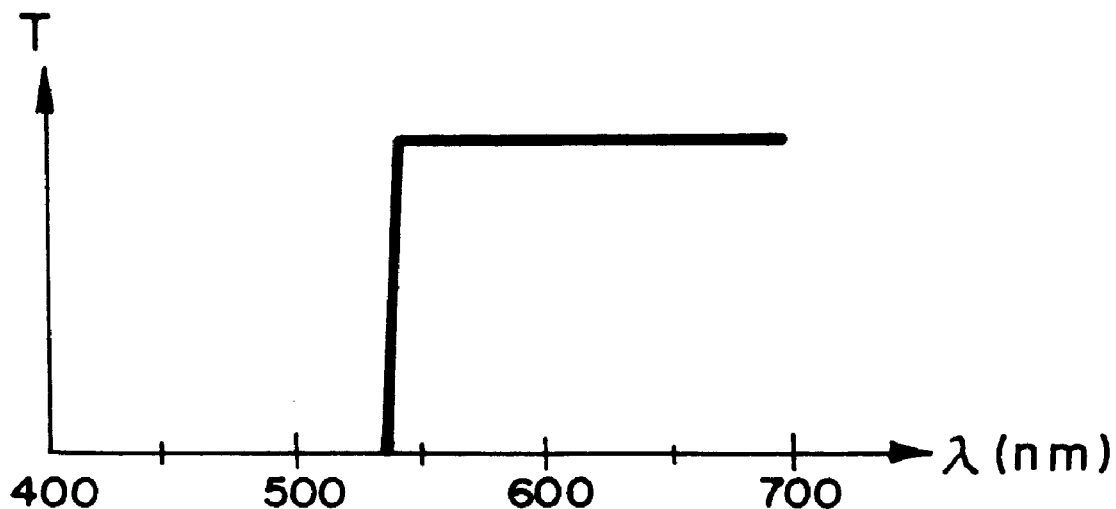

Now another example of an endoscope system provided with a fluorescence diagnosis system in accordance with the present invention will be described with reference to FIGS. 8, 9A and 9B, hereinbelow. In this example, auto fluorescence emitted from intrinsic pigment in the diagnostic part 10 upon excitation by the excitation light L1 without giving any fluorescence diagnosis agent to the diagnostic part 10 is detected and a division is carried out between a green auto fluorescence component and the long wavelength component. In FIG. 8, the components analogous to those shown in FIG. 5 are given the same reference numerals and will not be described here.

In FIG. 8, an endoscope system comprises an endoscope 100 which is inserted into a part of a patient which is to be observed, an illumination system 110 having an illuminating light source for emitting white illuminating light for a normal image and an excitation light source for emitting an excitation light, an optical path change-over unit 120 for switching the optical path between that for a normal image and that for a fluorescence image, a color CCD camera 130 which receives the white illuminating light reflected by the diagnostic part when a normal image is to be observed, a high speed camera unit 200 which receives fluorescence emitted from the diagnostic part upon excitation by the excitation light when a fluorescence image is to be observed, an image processing system 210 for processing the reflected light image or the fluorescence image, and a display 160 which reproduces the processed image information as a visible image.

The high speed camera unit 200 comprises a long pass filter 202 for cutting the excitation light L1 and a dichroic mirror 201 which separates the fluorescence L3 passing through the long pass filter 202 into a fluorescence component in a wavelength range in a green region (will be referred to as "the green region component", hereinbelow) and a component in a wavelength range longer than the green region (will be referred to as "the longer wavelength component", hereinbelow). The dichroic mirror 201 focuses the green region component on a first cooled CCD camera 205 and the longer wavelength component on a second cooled CCD camera 204.

The image processing system 210 comprises an A/D convertor 211 which digitizes image signals from the color CCD camera 130 and first and second cooled CCD cameras 205 and 204, a normal image memory 214 which stores the digitized normal image signal, a green fluorescence image memory 213 which stores a digitized image signal reflecting the green region component, a longer wavelength fluorescence image memory 212 which stores a digitized image signal reflecting the longer wavelength component, an adder memory 215 which adds the output of the green fluorescence image memory 213 to the output of the longer wavelength fluorescence image memory 212 and stores the sum, a divider memory 216 which divides the output of the green fluorescence image memory 213 by the output of the longer wavelength fluorescence image memory 212 and stores the result of the division, a video signal generating circuit 217 which carries out an image processing on the image signals stored in the normal image memory 214 and the divider memory 216 in order to display an image on the basis of the image signals, a timing controller 219 which outputs signals to the drivers 116, 123 and 143 for the illumination system 110, the high speed camera unit 200 and the optical path change-over unit 120, and a video processor 218 which controls the timing controller 219.

Operation of the endoscope system will be described hereinbelow. The operation of the endoscope system when a normal image is to be observed is the same as that in the preceding example and accordingly will not be described here.

When a fluorescence image is to be observed, the excitation light L1 is projected onto the diagnostic part 10 including the diseased part 11 in the same manner as in the preceding example. Fluorescence L3 emitted by the diagnostic part 10 upon excitation by the excitation light L1 is condensed by the objective lens 103 and travels toward the change-over mirror 121 in the change-over unit 120 through the image fiber 104 and the eyepiece 109 of the eyepiece unit 108. The change-over mirror 121 is driven by the driver 123 under the control of a signal from the timing controller 158 and is moved to the position shown by the broken line not to interrupt the fluorescence L3. The fluorescence L3 passes by the mirror 121 and travels toward the dichroic mirror 201 through the lens 203 and the long pass filter 202. The long pass filter 202 has transmission characteristics shown in FIG. 9A and transmits only fluorescence component having a wavelength not shorter than 480 nm, whereby the excitation light L1 whose central wavelength is 405 nm is cut. The dichroic mirror 201 has transmission characteristics shown in FIG. 9B and transmits the longer wavelength component in the wavelength range not shorter than 540 nm. The longer wavelength component passes through the dichroic mirror 201 and is focused on the first cooled CCD camera 205 and the green region component having a wavelength range of 480 nm to 540 nm is reflected by the dichroic mirror 201 and focused on the second cooled CCD camera 204.

The image signal reflecting the longer wavelength component obtained by the first cooled CCD camera 205 is input into the A/D convertor 211 and the image signal digitized by the A/D convertor 211 is stored in the longer wavelength fluorescence image memory 212. The image signal reflecting the green region component obtained by the second cooled CCD camera 204 is input into the A/D convertor 211 and the image signal digitized by the A/D convertor 211 is stored in the green fluorescence image memory 213.

The adder memory 215 adds the image signal reflecting the green region component stored in the green fluorescence image memory 213 to the image signal reflecting the longer wavelength component stored in the longer wavelength fluorescence image memory 212 and stores the sum image signal. The sum image signal corresponds to the whole visible auto fluorescence component and is equivalent to the image signal reflecting the whole visible auto fluorescence component in the preceding example.

Then the divider memory 216 divides the image signal reflecting the green region component stored in the green fluorescence image memory 213 by the image signal reflecting the whole visible auto fluorescence component stored in the adder memory 215 and stores the divided image signal. The divided image signal stored in the divider memory 216 is subjected to an encoding processing by the video signal generating circuit 217 after D/A conversion and then input into the display 160 to be reproduced as a visible image by the display 160. The normal image and the divided image may be overlaid.

Figure 10:
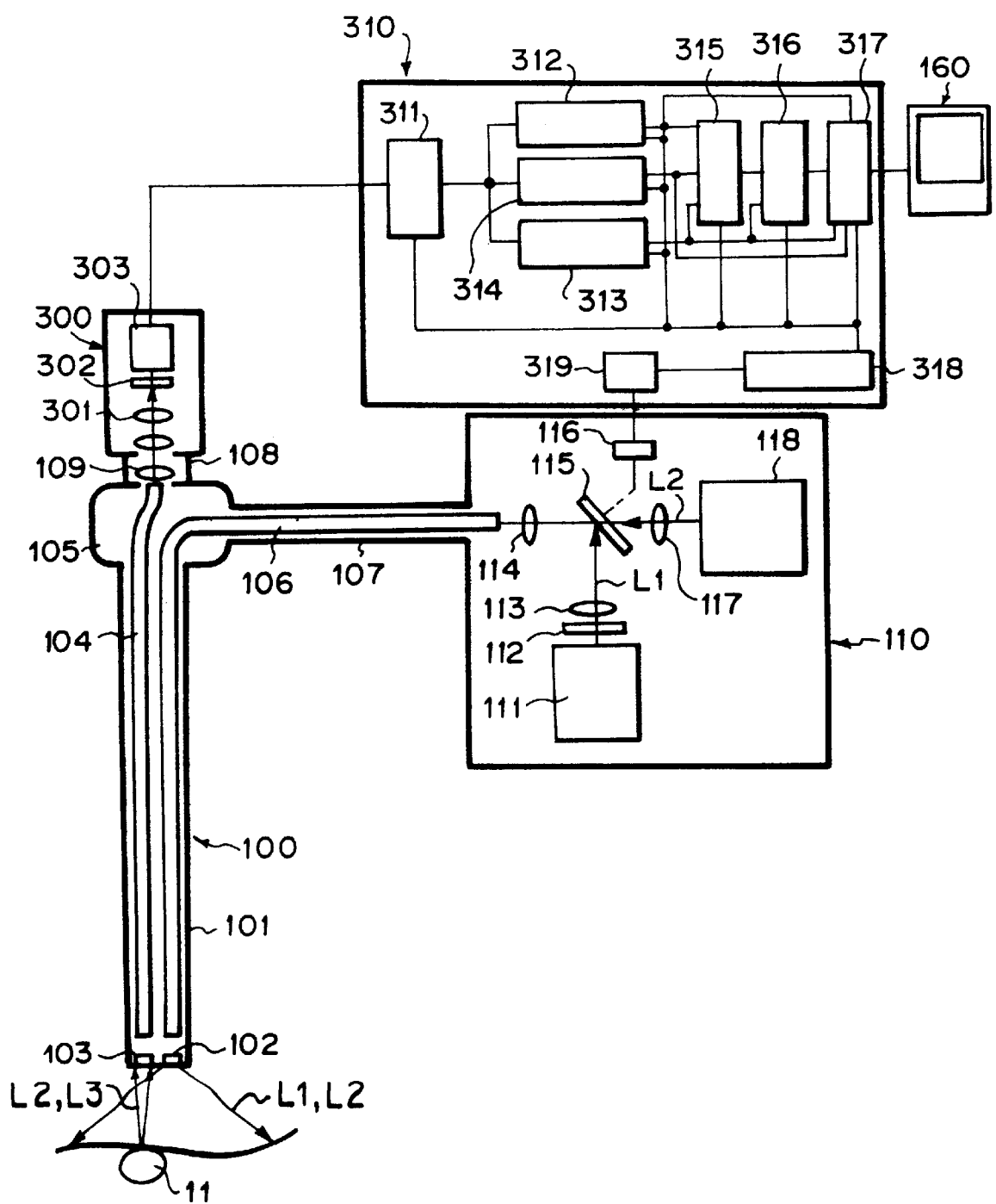
FIG. 10 is a schematic view showing still another example of an endoscope system provided with a fluorescence detecting system in accordance with the present invention, FIGS. 11A and 11B respectively show the color mosaic filter and the transmission characteristics of the respective sections of the filter, and FIGS. 12A and 12B respectively show a modification of the color mosaic filter and the transmission characteristics of the respective sections of the filter.

Now still another example of an endoscope system provided with a fluorescence diagnosis system in accordance with the present invention will be described with reference to FIGS. 10, 11A, 11B, 12A and 12B, hereinbelow. In this example, auto fluorescence emitted from intrinsic pigment in the diagnostic part 10 upon excitation by the excitation light L1 without giving any fluorescence diagnosis agent to the diagnostic part 10 is detected and a division is carried out between a green region component and a sum fluorescence component of a green region component and a red region component of the auto fluorescence. In FIG. 10, the components analogous to those shown in FIGS. 5 and 8 are given the same reference numerals and will not be described here.

In FIG. 10, an endoscope system comprises an endoscope 100 which is inserted into a part of a patient which is to be observed, an illumination system 110 having an illuminating light source for emitting white illuminating light for a normal image and an excitation light source for emitting an excitation light, an optical path change-over unit 120 for switching the optical path between that for a normal image and that for a fluorescence image, a color CCD camera 130 which receives the white illuminating light reflected by the diagnostic part when a normal image is to be observed, a high speed camera unit 300 which receives fluorescence emitted from the diagnostic part upon excitation by the excitation light when a fluorescence image is to be observed, an image processing system 310 for processing the reflected light image or the fluorescence image, and a display 160 which reproduces the processed image information as a visible image. The endoscope system of this example differs from those of the preceding examples in the structure and operation of the high speed camera unit 300 and the image processing system 310.

Figure 11A:
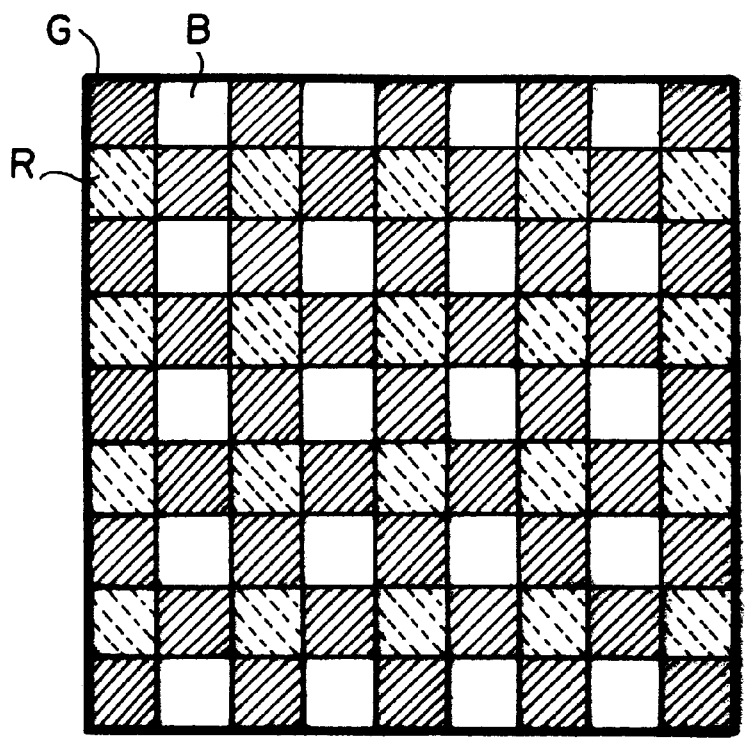

The high speed camera unit 300 comprises a excitation light cut filter 302 for cutting the excitation light component of the reflected light and the auto fluorescence L3 and a cooled CCD camera 303 on which an image is formed by the reflected light and the fluorescence L3 passing through the filter 302. A color mosaic filter shown in FIG. 11A is mounted on the light receiving face of the cooled CCD camera 303.

The image processing system 310 comprises an A/D convertor 311 which digitizes an image signal from the cooled CCD camera 303, red, green and blue image memories 314, 313 and 312 which respectively store red, green and blue components of the digitized image signal, an adder memory 315 which adds the green image signal stored in the green image memory 313 to the red image signal stored in the red image memory 314 and stores the sum, a divider memory 316 which divides the green image signal stored in the green image memory 313 by the red image signal stored in the red image memory 314 and stores the result of the division, a video signal generating circuit 317 which carries out an image processing on the image signals stored in the divider memory 316 in order to display an image on the basis of the image signal, a timing controller 319 which outputs signals to the drivers 116 and 123 for the illumination system 110 and the optical path change-over unit 120, and a video processor 318 which controls the timing controller 319.

Operation of the endoscope system will be described hereinbelow.

Figure 11B:
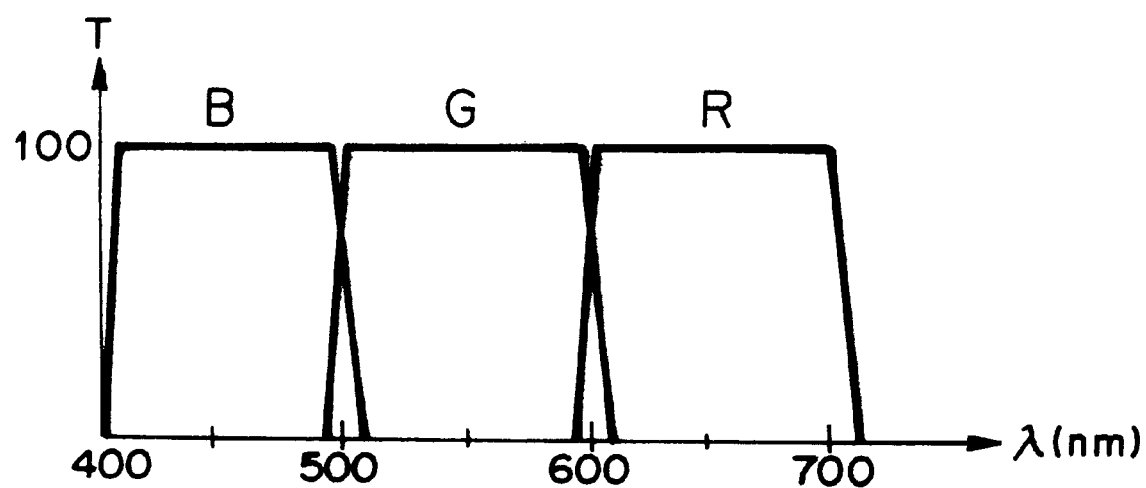

When a normal image is to be observed, the white light L2 is projected to illuminate the diagnostic part 10 as in the first example. A part of the white light L2 reflected by the diagnostic part 10 is condensed by the objective lens 103 and travels toward the high speed camera unit 300 through the image fiber 104 and the eyepiece 109 of the eyepiece unit 108. After passing through the eyepiece 109, the reflected light passes through a lens 301 and the excitation light cut filter 302 and is focused on the cooled CCD camera 303 through the color mosaic filter shown in FIG. 11A. The color mosaic filter comprises a plurality of red, green and blue sections whose transmission characteristics are as shown in FIG. 11B. That is, the red, green and blue filters transmit only the components in the wavelength ranges of respective colors. The image signal from the cooled CCD camera 303 is input into the A/D convertor 311 and the red, green and blue components of the digitized image signal are respectively stored in the red, green and blue image memories 314, 313 and 312. The normal image signals stored in the red, green and blue image memories 314, 313 and 312 are subjected to a color matrix processing and an encoding processing after D/A conversion by the video signal generating circuit 317, and then input into the display 160 to be reproduced as a visible image by the display 160.

When a fluorescence image is to be observed, the excitation light L1 is projected onto the diagnostic part 10 in the same manner as in the first example. Fluorescence L3 emitted by the diagnostic part 10 upon excitation by the excitation light L1 is condensed by the objective lens 103, travels through the image fiber 104, the eyepiece 109 and the excitation light cut filter 302 and then focused on the cooled CCD camera 303. Since the intensity of the fluorescence L3 is very weak as compared with the reflected light, the image taking speed should be sufficiently lowered when a normal image is to be observed as compared with when a fluorescence image is to be observed.

As when a normal image is to be observed, the image signal from the cooled CCD camera 303 is input into the A/D convertor 311 and the red, green and blue components of the digitized image signal are respectively stored in the red, green and blue image memories 314, 313 and 312. Then the adder memory 515 adds the image signal reflecting the green region component stored in the green image memory 313 to the image signal reflecting the red region component stored in the red image memory 313 and stores the sum image signal.

Then the divider memory 316 divides the image signal reflecting the green region component stored in the green image memory 313 by the image signal stored in the adder memory 315 and stores the divided image signal. The divided image signal stored in the divider memory 316 is subjected to a color matrix processing and an encoding processing by the video signal generating circuit 317 after D/A conversion and then input into the display 160 to be reproduced as a visible image by the display 160. When memories for storing red, green and blue image signals for a normal image is provided separately from the memories 312 to 314, the normal image and the divided image can be overlaid.

It is possible to add up the image signals respectively representing the red, green and blue fluorescence components respectively stored in the memories 314, 313.and 312, store the sum in the adder memory 315 as an image signal reflecting the whole visible auto fluorescence component and divide the image signal stored in the green image memory 313 by the image signal stored in the adder memory 315.

Figure 12A:
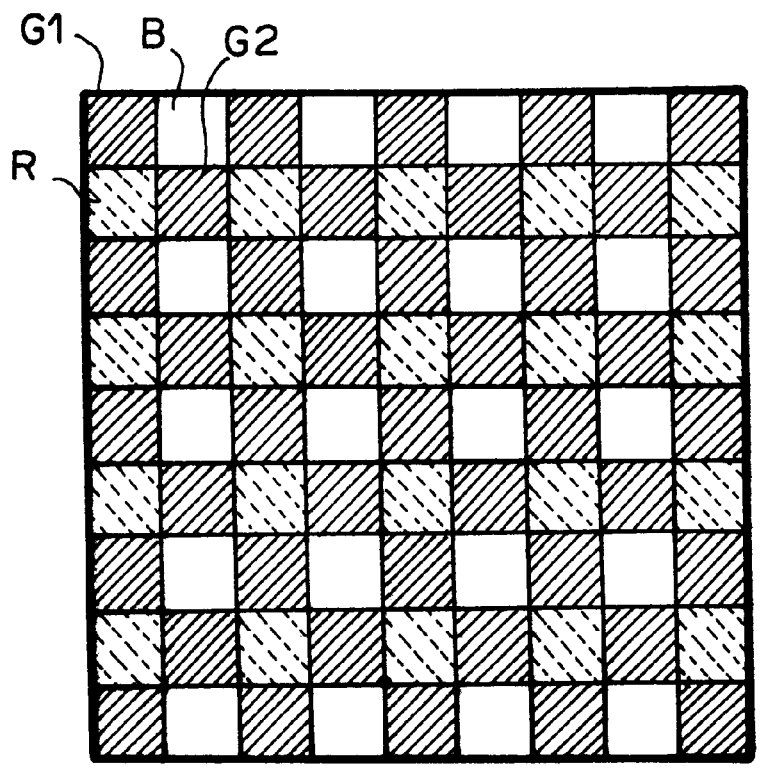
Figure 12B:
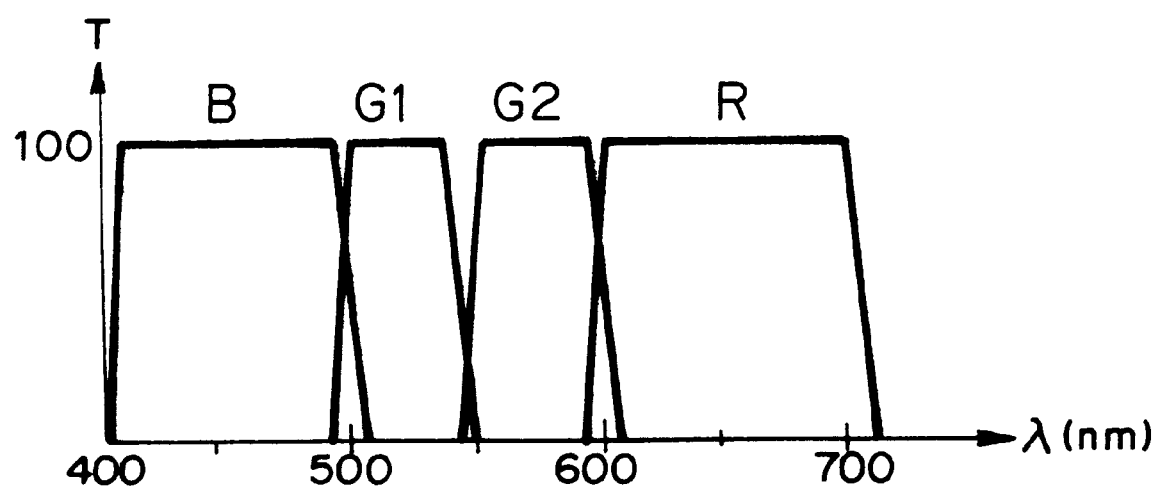

Further when a color mosaic filter shown in FIG. 12A having a plurality of sections whose transmission characteristics are as shown in FIG. 12B is employed in place of the color mosaic filter shown in FIG. 11A, it is possible to carry out, for instance, a division (G1 fluorescence image)/(R fluorescence image+G1 fluorescence image+G2 fluorescence image+B fluorescence image).

Further in the endoscope systems described above, since the high speed camera unit is simple in structure, it can be applied to an electronic endoscope where an image taking device is provided on the tip of the endoscope.

Further though, in the embodiment described above, the fluorescence detecting system in accordance with the present invention is applied to an image taking system, the present invention can be applied also to an optical scanning system. In this case, fluctuation in the detecting efficiency ηD depending upon the distance between the light emitting point and the photodetector can be cancelled.

What is claimed is:

1. A fluorescence detecting system for detecting auto fluorescence emitted from an intrinsic pigment in a part of an organism to be observed comprising an excitation light projecting means which projects onto the part to be observed excitation light in the wavelength range which can excite the intrinsic pigment of the organism to emit auto fluorescence, a first fluorescence detecting means which extracts from the auto fluorescence emitted from the pigment a whole auto fluorescence component in a visible region having a predetermined wavelength range including a first relatively short wavelength range and a relatively long wavelength range, a second fluorescence detecting means which extracts an auto fluorescence component in a second relatively short wavelength range in the visible region from the auto fluorescence, and a divider means which carries out a division between the auto fluorescence components respectively extracted by the first and second fluorescence detecting means.

2. A fluorescence detecting system as defined in claim 1 in which each of the first and second fluorescence detecting means two-dimensionally detects the fluorescence emitted from the part to be observed and takes a fluorescence image of the part.

3. A fluorescence detecting system for detecting auto fluorescence emitted from an intrinsic pigment in a part of an organism to be observed comprising an excitation light projecting means which projects onto the part to be observed excitation light in the wavelength range which can excite the intrinsic pigment of the organism to emit auto fluorescence, a first fluorescence detecting means which extracts from the auto fluorescence emitted from the pigment a sum fluorescence component of a fluorescence component in a predetermined short wavelength range in a first relatively short wavelength range and a fluorescence component in a predetermined wavelength range in a relatively long wavelength range, a second fluorescence detecting means which extracts from the auto fluorescence an auto fluorescence component in a second relatively short wavelength range, and a divider means which carries out a division between the sum fluorescence component extracted by the first fluorescence detecting means and the fluorescence component extracted by the second fluorescence detecting means.

4. A fluorescence detecting system as defined in claim 3 in which each of the first and second fluorescence detecting means two-dimensionally detects the fluorescence emitted from the part to be observed and takes a fluorescence image of the part.

* * * * *